(12) United States Patent
Miller et al.

(10) Patent No.: US 6,252,063 B1
(45) Date of Patent: Jun. 26, 2001

(54) CRYSTALLINE SALTS OF A CARBAPENEM ANTIBIOTIC

(75) Inventors: Ross A. Miller, Fanwood; Scott S. Ceglia, Woodbridge, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/432,864

(22) Filed: Nov. 2, 1999

Related U.S. Application Data

(60) Provisional application No. 60/110,345, filed on Dec. 1, 1998.

(51) Int. Cl.[7] ............... A61K 31/4995; C07D 477/08; C07D 477/14
(52) U.S. Cl. .............................................. 540/302
(58) Field of Search .............................. 504/302

(56) References Cited

U.S. PATENT DOCUMENTS 5,756,725  5/1998  Wilkening et al. ............ 540/302

*Primary Examiner*—Mark L. Berch
(74) *Attorney, Agent, or Firm*—Sylvia A. Ayler; Mark R. Daniel

(57) ABSTRACT

Crystalline salts of an amorphous, unstable carbapenem antibiotic having the formula:

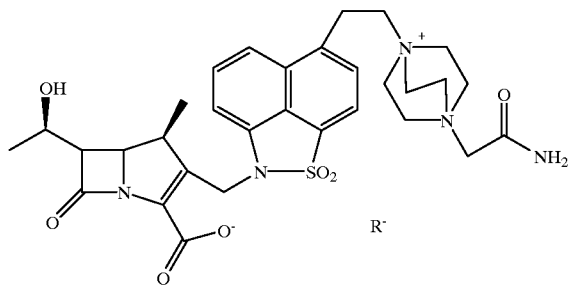

are disclosed, wherein $R^-$ represents beyslate, tosylate, napsylate, saccharate or alizarate.

6 Claims, No Drawings

CRYSTALLINE SALTS OF A CARBAPENEM ANTIBIOTIC

This application claims the benefit of U.S. Provisional Application No. 60/110,345, filed Dec. 1, 1998.

BACKGROUND OF THE INVENTION

The carbapenem antibiotic designated herein as Compound I:

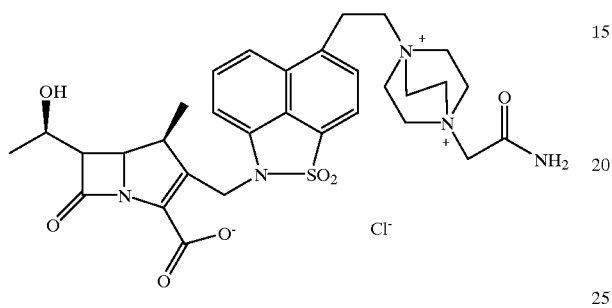

is disclosed in U.S. Pat. No. 5,756,725 (WO 97/40048) and has been shown to be a highly effective, broad spectrum antibiotic. However, formulation of this compound into a form suitable for the market place has been hampered by the unavailability of a stable crystalline form.

Prior to this invention, purification of Compound I was performed by column chromatography and the thermally and hydrolytically unstable amorphous chloride or triflate salt forms and their formulations had to be stored at low temperatures. Now with the present invention there are provided non-hygroscopic, thermally stable, crystalline salts readily obtainable by a crystallization process which serves to purify the product as well, thus, avoiding the use of chromatographic techniques.

SUMMARY OF THE INVENTION

This invention is concerned with highly stable crystalline salts of Compound I and processes for their preparation, which processes incidentally serve to purify Compound I, especially by removal of palladium, ruthenium and tin contaminants.

The invention is also concerned with pharmaceutical formulations comprising one of the salts of Compound I as active ingredient.

It is also concerned with a method of treating infections with the salts of this invention.

DETAILED DESCRIPTION OF THE INVENTION

The Compound I salts of this invention are as shown below:

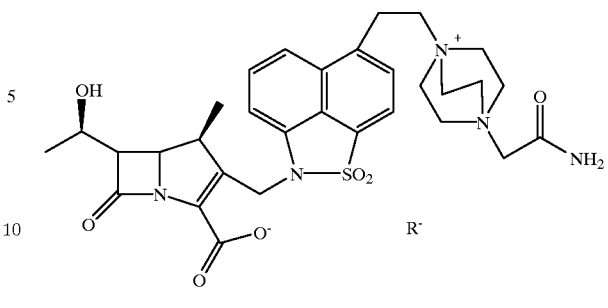

wherein R⁻ is selected from:

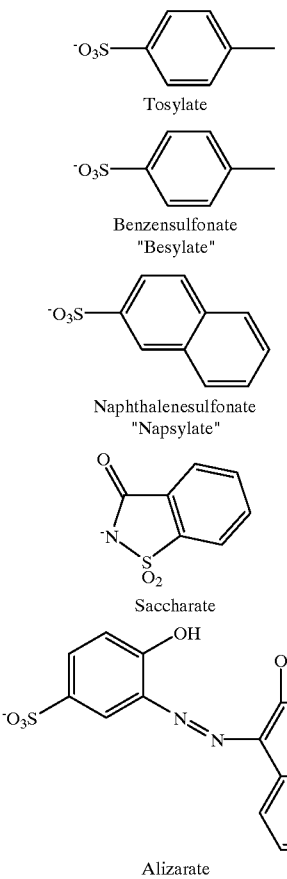

Each of these salt forming anions is well known in the art and known to be non-toxic and pharmaceutically acceptable.

A process for the preparation of the salts of this invention comprises treating a solution of Compound I with an alkali metal salt of formula M⁺R⁻, wherein M⁺ is an alkali metal cation. A group of alkali metal cations includes sodium (Na⁺), potassium (K⁺) and cesium (Cs⁺). A sub-group includes Na⁺ and K⁺, and exemplary of this sub-group is Na⁺.

The counter ion associated with Compound I forming the starting material for the process of this invention includes any counter ion, X⁻, that will provide a water soluble salt thereof. A group of such counter ions includes chloride, triflate, hemisulfate, mopsylate (4-morpholinepropanesulfonate), bromide, acetate and mesylate. A sub-group includes chloride and triflate. Exemplary of this sub-group is triflate.

The temperature at which the reaction is conducted is not critical. However, because of the limited stability of the Compound I starting material, the reaction temperature should be maintained at about 5 to about 25° C., and room temperature (about 15 to about 25° C.) is convenient.

In one embodiment of the process of this invention, a solution of Compound I suitable for treatment with the alkali metal salt MR is obtained in the last step in the synthesis of Compound I which involves the hydrogenolysis of an activated ester of Compound I such as the p-nitrotoluyl, benzyl, allyloxy, or p-methoxybenzyl ester.

EXAMPLE

Hydrogenation of Penultimate Bis Triflate and Crystallization of the Benzenesulfonate Salt

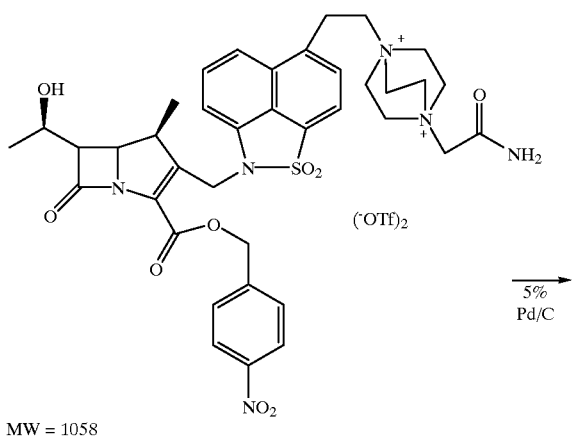

MW = 1058

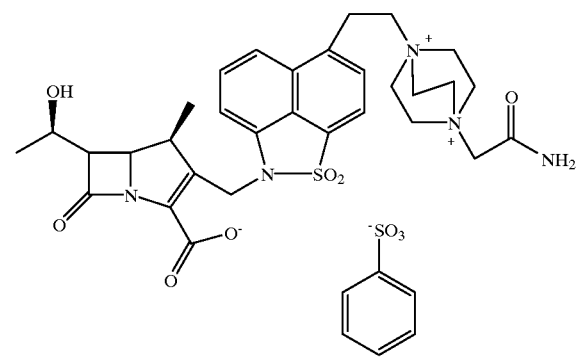

MW = 783

| Materials | Amt. | | Mole | MW |
|---|---|---|---|---|
| Penultimate Bis Triflate | 5000 | g | 4.73 | 1058 |
| 5% Pd/C | 1250 | g | | |
| Isopropanol | 58 | L | | |
| 4-Morpholinepropanesulfonic acid | 2971 | g | 14.2 | 209.26 |
| 5N NaOH | 1.42 | L | 7.1 | |
| Toluene | 30 | L | | |
| Water | 126 | L | | |
| Sodium Benzenesulfonate | 12.5 | kg | | |

A buffered solution of 4-morpholinepropanesulfonic acid was prepared by dissolving 2941 g in 58 L water followed by addition of approximately 1.4 L 5N NaOH, resulting in a final solution pH of 7.2.

This solution was then added to 5000 g of penultimate bis triflate, and then 58 L isopropanol was added. The resulting pH of the slurry was 6.9.

The mixture was degassed and then 1250 g 5% Pd/C added and the system placed under hydrogen (40 psi) until the reaction was done. The resulting pH of the solution after reaction was 6.3.

The catalyst was filtered off and the cake slurry washed with 25 L water. The filtrate was immediately cooled to 5° C. to improve the stability of the Compound I cation.

The filtrate was washed with toluene (25 L) and the layers separated. The separation was done at 5–10° C., gave a clean cut, but required a 15 minute age to settle.

The washed filtrate was added to a solution of sodium benzenesulfonate (12.5 kg) in 37.5 L water at 20° C.

The filtrate and aqueous sodium benzenesulfonate were added via a syringe equipped with a 0.45 um syringe filter to remove nefloss. The pH of the aq. sodium benzenesulfonate solution was checked before adding the washed filtrate and adjusted to 6.3 with an appropriate amount of 0.002M TfOH solution.

The resulting slurry was cooled to 5° C. and filtered, slurry washed with 1:1 IPA:water and then water.

The solid was dried under nitrogen at ambient temperature.

Employing the procedure substantially as described in the above EXAMPLE, but substituting for the sodium benzenesulfonate used therein, an equimolar amount of an alkali metal salt of an ion, $R^-$, wherein $R^-$ is selected from tosylate, napsylate, saccharate and alizarate, there was produced the corresponding salt of Compound I.

A comparison of the stabilities of certain of the crystalline salts of this invention and certain amorphous salts is shown in the following Table;

TABLE

| COMPOUND | INCREASE IN A% TOTAL IMPURITIES | DECOMPOSITION RATE A%/HR |
|---|---|---|
| Compound I chloride | 0.8 | 1.6 |
| 30 min. @ 80° C. | | |
| Compound I hemisulfate | | |
| 25 min @ 80° C. | 1.1 | 2.7 |
| 120 min @ 80° C. | 5.4 | |
| Compound I besylate | | |
| 120 min @ 120° C. | 0.05 | 0.03 |
| Compound I saccharate | | |
| 60 min @ 80° C. | 0.15 | 0.15 |

As can be seen from the Table, the normal decomposition rate of the lyophilized chloride solid is about 1.6 A% per hour at 80° C. The hemisulfate is somewhat less stable at this temperature. However, in complete contrast, the benzenesulfonate is remarkably stable even at 100° C. for 2 hours (less than 0.03 A% degradation per hour).

Additionally, the besylate is non-hygroscopic at 20, 40, 60 and 90% humidity over 1 week.

What is claimed:
1. A compound of structural formula:

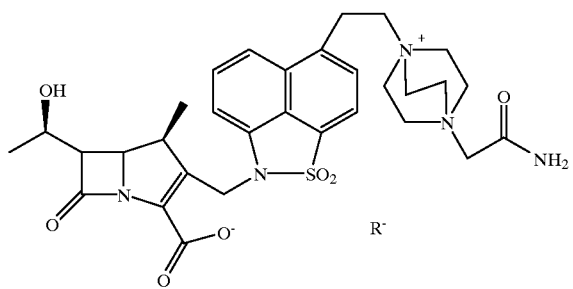

wherein R⁻ represents besylate, tosylate, napsylate, saccharate or alizarate.

2. The compound of claim 1 wherein R⁻ represents besylate.

3. A process for the preparation of the compound of formula:

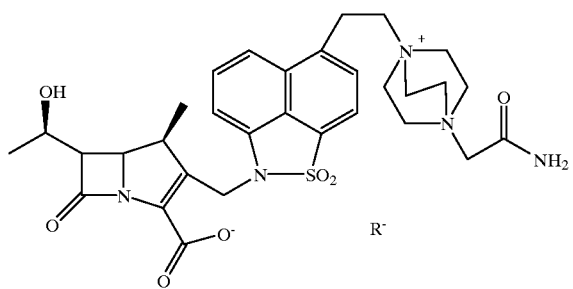

wherein R⁻ represents besylate, napsylate, tosylate, saccharate and alizarate, which comprises treating an aqueous solution of a starting material of formula:

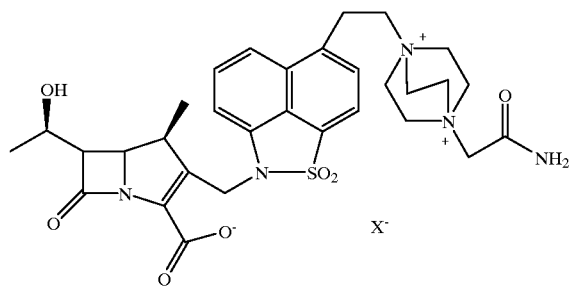

with an alkali metal salt of formula M⁺R⁻, wherein M⁺ is an alkali metal cation, and wherein X⁻ is a counter ion that provides water solubility to the starting material.

4. The process of claim 3 wherein the alkali metal cation is Na⁺, K⁺ or Cs⁺ and the X⁻ is chloride, triflate, hemisulfate, (4-morpholinepropanesulfonate), bromide, mesylate or acetate.

5. The process of claim 4, wherein X⁻ is triflate.

6. The process of claim 5 wherein the starting material is obtained from the final step of the process for the synthesis of Compound I comprising the hydrogenolysis of an activated ester as follows:

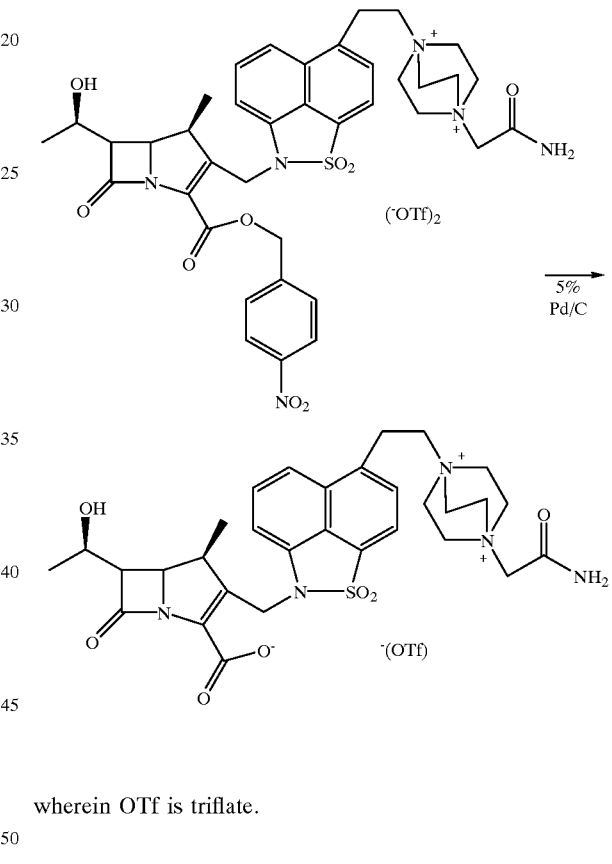

wherein OTf is triflate.

* * * * *